United States Patent
Dal Farra et al.

(10) Patent No.: US 9,199,101 B2
(45) Date of Patent: Dec. 1, 2015

(54) USE OF A PEPTIDE HYDROLYSATE OF PEA AS MOISTURIZING ACTIVE AGENT

(75) Inventors: Claude Dal Farra, Kerhonkson, NY (US); Nouha Domloge, Valbonne (FR); Jean-Marie Botto, Valbonne (FR)

(73) Assignee: ISP INVESTMENTS INC., Wilmington, DE (US)

( * ) Notice: Subject to any disclaimer, the term of this patent is extended or adjusted under 35 U.S.C. 154(b) by 49 days.

(21) Appl. No.: 13/640,827

(22) PCT Filed: Apr. 14, 2011

(86) PCT No.: PCT/FR2011/000219
§ 371 (c)(1),
(2), (4) Date: Oct. 12, 2012

(87) PCT Pub. No.: WO2011/128530
PCT Pub. Date: Oct. 20, 2011

(65) Prior Publication Data
US 2013/0029917 A1 Jan. 31, 2013

(30) Foreign Application Priority Data
Apr. 15, 2010 (FR) .................................. 10 001604

(51) Int. Cl.
*A61K 8/97* (2006.01)
*A61K 36/48* (2006.01)
*A61Q 19/00* (2006.01)
*A61Q 19/08* (2006.01)

(52) U.S. Cl.
CPC . *A61Q 19/00* (2013.01); *A61K 8/97* (2013.01); *A61K 36/48* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 5,153,230 | A * | 10/1992 | Jaffery | 514/458 |
| 5,382,431 | A * | 1/1995 | Pickart | 424/401 |
| 7,060,693 | B1 | 6/2006 | Dumas et al. | |
| 2004/0234560 | A1 * | 11/2004 | Kimura et al. | 424/401 |

FOREIGN PATENT DOCUMENTS

| | | |
|---|---|---|
| EP | 2033617 | 3/2009 |
| FR | 2801504 | 6/2001 |
| FR | 2874502 | 3/2006 |
| FR | 2904556 | 2/2008 |
| JP | 09-025225 | 1/1997 |
| JP | 2008-100929 | 5/2008 |
| JP | 2008-100930 | 5/2008 |
| WO | WO8602833 | 5/1986 |
| WO | WO02055049 | 7/2002 |
| WO | WO 02102347 A2 * | 12/2002 |
| WO | WO 2006078067 A1 * | 7/2006 |
| WO | 2008/015341 A2 | 2/2008 |
| WO | WO2008015341 * | 2/2008 |
| WO | WO2008151890 | 12/2008 |

OTHER PUBLICATIONS

Magalhaes, Paulo J. et al; "Isolation of phenolic compounds from hop extracts using polyvinylpolypyrrolidone: characterization by high performance liquid chromatography-diode array detection-electrospray tandem mass spectrometry." J. Chrom. A (2010) 1217 p. 3258-3268, available online Oct. 30, 2009.*
Deng, Xiaohu et al; "Preparation and charactrization of actrive carbon adsorbents for wastewater treatment from elutrilithe." J. Colloid. Interface.Sci. (1997) 192 p. 475-480.*
Lenaz, Giorgio et al; "Mitochondria, oxidative stress, and antioxidant defences." Acta Biochimica Polonica (1999) 46(1) p. 1-21.*
Machine translation of WO 02102347.*
Machine translation of WO 2006078067.*
Sammour, R. H.; "Molecular reassessment of relationships within vicieae using electrophoretic and immunochemical techniques." Afr. Crop Sci. J. (2005) 13(1) p. 27-39.*
How, J. S. L. and Morr, C. V.; "Removal of phenolic compounds from soy protein extracts using activated carbon." J. Food. Sci. (1982) 47(3) p. 933-940).*
The OHSA chemical sampling sheets for hexane (https://www.osha.gov/dts/chemicalsampling/data/CH_245400.html, downloaded Oct. 8, 2014).*
The OSHA chemical sampling sheet for methanol (https://www.osha.gov/dts/chemicalsampling/data/CH_251600.html, downloaded Oct. 8, 2014).*
The OSHA chemical sampling sheet for chloroform (https://www.osha.gov/dts/chemicalsampling/data/CH_227600.html, downloaded Oct. 8, 2014).*
Machine translation of WO2008015341.*
Kawesia et al., "Interaction between transcellular and paracellular water transport pathways through aquaporin 5 and the tight junction complex". PNAS Feb. 27, 2007.
Sougrat et al., "Functional Expression of AQP3 in Human Skin Epidermis and Reconstructed Epidermis". Yje Society for Investigate Dermatology, Inc. Apr. 4, 2002.
International Search Report, PCT/FR2011/000219, published on Oct. 20, 2011.
International Search Report ( English translation), International Application No. PCT/FR2011/000219 (mailed Aug. 30, 2011, published Aug. 20, 2011).

(Continued)

Primary Examiner — Maury Audet
Assistant Examiner — Fred Reynolds
(74) Attorney, Agent, or Firm — Thompson Hine LLP

(57) ABSTRACT

The invention relates to the cosmetic use of a peptide hydrolysate of pea (*Pisum sativum* L.), as skin-moisturizing active agent. The invention also relates to the use of a cosmetic composition comprising an effective amount of active agent according to the invention in a physiologically acceptable medium, for preventing dryness of the skin or restoring moisturization of the skin. The invention also relates to the use of this novel active agent for preparing a pharmaceutical, in particular dermatological, composition intended for treating pathological dryness of the skin.

9 Claims, No Drawings

(56) References Cited

OTHER PUBLICATIONS

Written Opinion (English translation), International Application No. PCT/FR2011/000219 (mailed Aug. 30, 2011).

Silbert, J.E., "Proteoglycans and Glycosaminoglycans," *Biochemistry and Physiology of the Skin*, Goldsmith, L.A. (ed.), Oxford University Press, 1983, pp. 448-461.

Dumas, M. et al., "Hydrating Skin by Stimulating Biosynthesis of Aquaporins," *Journal of Drugs in Dermatology*, pp. s20-s24 (2007).

* cited by examiner

USE OF A PEPTIDE HYDROLYSATE OF PEA AS MOISTURIZING ACTIVE AGENT

CROSS REFERENCE TO RELATED APPLICATIONS

This application is the national stage of PCT Application No. PCT/FR2011/000219 filed Apr. 14, 2011, which claims priority from French Patent Application No. 1001604, filed Apr. 15, 2010, the entire disclosures of which are hereby incorporated in their entirety.

FIELD OF THE INVENTION

The present invention is in the field of cosmetics, and pharmaceuticals, and more specifically in the field of dermatology. The invention relates to the cosmetic use of a peptide hydrolysate of pea (*Pisum sativum* L.) as a moisturizing active agent. The invention relates more specifically to the cosmetic use of a peptide hydrolysate of pea (*Pisum sativum* L.) to improve the constituent moisturization of skin, due to its ability to activate aquaporin expression, glycosaminoglycan expression and filaggrin expression.

The invention also relates to a cosmetic treatment process designed to restore the water imbalance which occurs during cutaneous ageing.

The active agent can be used on its own or in combination with other active agents.

The invention also relates to the use of this novel active agent for creating a pharmaceutical, and in particular dermatological, composition designed to prevent or treat pathological dryness of the skin.

BACKGROUND OF THE INVENTION

The skin is a vital organ composed of several layers (dermis, proliferative layers and stratum corneum), which covers the entire surface of the body and essentially serves as a barrier to the external environment. The quality and high functionality of the skin are directly linked to the water content of the different layers of the epidermis and the dermis. Thus, in a normal epidermis, the proliferative layers contain approximately 70% water, whereas the stratum corneum only contains 10 to 15% water.

Moisturization of the skin depends on three factors: the water supply provided by the circulation of physiological fluids, the loss of water to the external environment and finally the capacity of the various parts of the skin for containing water molecules.

The water supply is regulated by hormones (aldosterone, sexual hormones), pH or osmotic variations. Cellular membranes are inherently hydrophobic and therefore have low water-permeability, but there are water channels, namely pores which facilitate the flow of water and certain solutes.

Aquaporins are a type of transmembrane protein for transporting water and small molecules in solution. Type-3 aquaporins, or AQP3s, are present in the human epidermis, and more specifically in the keratinocytes of the proliferative layers of the epidermis (R. Sougrat et al., J. Invest. Dermatol., 2002). They are capable of transporting water and glycerol, the latter playing an important role in the constitution of the hydrolipidic film on the surface as well as maintaining the suppleness and sensory qualities of the stratum corneum. The moisturization and AQP3 content of the keratinocytes are directly linked. Thus, increasing AQP3s in the skin enables better moisturization of the epidermis (M. Dumas, J. Drugs Dermatol., 6 Jun. 2007). On the other hand, aquaporins play a role in the barrier function by positively regulating the establishment of links and tight-junction cellular communication (J. Kawedia et al., PNAS 104(9), 2007).

The corneal layers (strata cornea) form a barrier which is essential for limiting water loss. In the deepest layers of the stratum corneum, during the formation of corneocytes, insoluble profilaggrin present in granular keratinocytes turns into filaggrin and thus becomes capable of connecting to keratin fibers to form microfibrils. Filaggrin is also involved in maintaining the water content of the corneal layers. What will happen to it during corneocyte maturity depends on the water gradient in the stratum corneum. In normal skin, when there is low ambient humidity, filaggrin is hydrolyzed and releases hygroscopic and soluble substances composed of amino acids and amino acid derivatives which are part of the "Natural Moisturizing Factor", or NMF. The NMF is able to collect water from the atmosphere and retain the water in the stratum corneum so as to maintain supple and flexible skin, and to allow the enzymatic reactions which are necessary for the corneocytes to evolve towards the final stage of desquamation. However, in certain conditions (e.g. xerosis, atopy), or even when the skin is aged, the NFM is of an insufficient quantity to ensure moisturizing functions or it can undergo degradation or cross over the cellular membrane, allowing the water to escape gradually, which evaporates in the external environment.

However, the main water reserves can be found in the dermis, which contains up to 80% water when the skin is young (this proportion is reduced with age). Dermal water derives from plasma and is directly linked to glycosaminoglycans (GAGs) and structural glycoproteins. The main function of the glycosaminoglycans is to ensure the structuring of collagen and elastin fibers. Hyaluronic acid is the most abundant glycosaminoglycan in the skin. It is the main component of the dermis and is also present around the keratinocytes in the epidermis. GAGs are incredibly hygroscopic molecules which are able to retain up to one thousand times their weight in water (J E. Silbert, Proteoglycans and glycosaminoglycans. In: Goldsmith L A, ed. Biochemistry and Physiology of the Skin. New York, N.Y.: Oxford University; 1983: 448-461). Due to these exceptional properties, glycosaminoglycan and collagen complexes are the main agents for storing water in the extracellular matrices.

Cutaneous water loss can have several origins: hereditary, acquired or environmental. In a very dry environment, water loss by evaporation from the stratum corneum is significant and can exceed the rate of replacement by transcellular diffusion.

During cutaneous ageing, the skin becomes dry. Thus, it is very often observed among older subjects, in particular those over the age of 50, that xerosis or the drying up of mucus membranes linked to a lower level of sebum secretion, to changes in hormone levels or to a slowing down in water flow across the epidermis, manifests. The skin is therefore the main location for itching and tautness, two symptoms which are characteristic of dry skin. Xerosis induced by photochemotherapy and eczema are examples of acquired conditions manifesting in dryness of skin. Sjögren's Syndrome or neck radiotherapy can be cited as examples of acquired conditions which result in dryness of the mouth, or xerostomia. Finally ocular or vaginal dryness are examples of conditions involving a drying of mucus membranes.

A first alternative for treating dry skin consists of topically administering products designed for restoring the cutaneous barrier, or film-forming agents designed to retain water. However, these products act superficially and do not correct the biological defects of skin suffering from chronic dehydration.

FR 2 801 504 and FR 2 874 502 can also be cited, which describe the use of plant extracts to stimulate aquaporin activity and to improve skin moisturization. Despite everything, these active ingredients do not allow an improvement in the constituent moisturization of all the parts of the skin. Peptide extracts of pea have been described for their pigmenting effect (FR 2 904 556) or their desquamation effect (JP 09025225), but have never described the beneficial effect on skin moisturization.

The inventors have now shown that the use of a peptide hydrolysate of pea (*Pisum sativum* L.) as an active agent capable of activating the expression of aquaporins, glycosaminoglycans and filaggrin, produces an overall improvement in the constituent moisturization of skin.

DESCRIPTION OF THE INVENTION

The main object of the present invention is a novel use of a peptide hydrolysate of pea (*Pisum sativum* L.) as a skin-moisturizing active agent.

Skin is understood to be the collection of covering tissues constituting the skin and mucus membranes, including the scalp.

It is clear that the invention is designed for mammals in general, and more specifically for human beings.

The inventors have indeed identified biological activities which are useful for improving constituent moisturization of skin, a peptide hydrolysate of pea.

The characteristic useful biological activities according to the invention are defined in vitro by the capacity of the hydrolysate of pea to increase the expression of aquaporins, glycosaminoglycans and filaggrin.

"Active agent capable of improving the expression of aquaporins, glycosaminoglycans and filaggrin" is understood to be any substance which is capable of improving the protein synthesis of these compounds by directly or indirectly modulating gene expression or by means of other biological processes such as post-translational assembly or protein stabilization.

According to the present invention, it is preferable for the aquaporin to be type-3 aquaporin, or AQP3, which is present in keratinocyte membranes.

The invention relates more specifically to the cosmetic use of a peptide hydrolysate of pea (*Pisum sativum* L.) to improve the constituent moisturization of skin, due to its positive effect on water flow and the improvement in the capacity for storing water in the corneal layer, the basal layers of the epidermis, and the dermis.

"Constituent moisturization" is understood to be the water content linked to all the parts of the skin, that is to say the dermis, the basal layers of the epidermis (or the proliferative epidermis) and the corneal layer.

"Peptide hydrolysate" is understood to be a mixture of compounds which are primarily represented by peptides.

"Topical application" is understood to be the application or spreading of the active agent according to the invention, or a composition containing said agent, on the surface of the skin or a mucus membrane.

It is understood by "physiologically acceptable" that the active agent according to the invention, or a composition containing said agent, is suitable for coming into contact with the skin or a mucus membrane without provoking a toxicity or intolerance reaction.

The active agent according to the invention can be obtained by extracting plant-based proteins, following by controlled hydrolysis which releases biologically active peptide fragments.

A large number of proteins found in plants are likely to contain biologically active peptide fragments within their structure. The controlled hydrolysis enables these peptide fragments to be released. To embody the invention, it is possible, but not necessary, to extract the proteins in question first and then to hydrolyze them, or to carry out hydrolysis on a raw extract first and then purify the peptide fragments. It is also possible to use certain hydrolyzed extracts without purifying the peptide fragments corresponding to the biologically active peptides according to the invention, while nonetheless ensuring the presence of said fragments by using the appropriate analytical means.

The entire plant, or a specific part of the plant (leaf, seed, etc.), can be used to carry out extraction.

More specifically according to the invention, plant seeds from the fabaceae family (legumes), of the pea species *Pisum sativum* L, are used. The term "pea" also includes the seeds, which are themselves rich in protein (25%).

All methods of extraction or purification known to the person skilled in the art can be used for the preparation of hydrolysate according to the invention.

In a first stage, the seeds are ground using a plant grinder. The powder obtained thus can subsequently be "delipidated" by means of a standard organic solvent (such as an alcohol, hexane or acetone).

Then the proteins are extracted by adhering to the (modified) standard process (Osborne, 1924); the ground plant material is suspended in an alkaline solution containing an insoluble (0.01-20%) adsorbent product of type polyvinylpolypyrrolidone (PVPP); indeed, it was observed that the hydrolysis operations and subsequent purifications were facilitated by this means. In particular, the concentration of phenolic substances interacting with the proteins was clearly lower.

The soluble portion, containing the proteins, carbohydrates and possibly lipids, is collected after the stages of centrifugation and filtration. This raw solution is then hydrolyzed under controlled conditions to produce soluble peptides. Hydrolysis is defined as being a chemical reaction wherein a molecule is split by water, this reaction being able to take place in a neutral, acidic or basic medium. According to the invention, hydrolysis is carried out chemically and/or advantageously by proteolytic enzymes. The use of plant-based endoproteases (papain, bromelain, ficin) and micro-organisms (*Aspergillus, Rhizopus, Bacillus* etc.) can therefore be cited here. For the same reasons as before, i.e. to eliminate polyphenolic substances, a quantity of polyvinylpolypyrrolidone is added to the reaction medium during this controlled hydrolysis stage. After thermal deactivation of the enzymes and filtration, which allows the residual enzymes and polymers to be eliminated, the obtained filtrate (solution) is purified again so as to select the peptide compounds with a low molecular weight. The splitting can occur advantageously via ultrafiltration and/or via a chromatographic method.

At this stage, the hydrolysate of pea is characterized by a dry weight of 70 to 80 g/kg, a protein level of 55 to 65 g/l, a sugar level of 2 to 5 g/l and a polyphenol level of 1 to 3 g/l.

The hydrolysate obtained according to the invention is qualitatively and quantitatively analyzed, using the typical techniques well known to the person skilled in the art, for its physicochemical characteristics and its protein and peptide compound content. The hydrolysate obtained is composed of peptides with a molecular weight of less than 5 kDa.

The next stage is the dilution phase in water or in any mixture of aqueous solvents. Thus, the active agent according to the invention is advantageously solubilized in one or more physiologically acceptable solvents, such as water, glycerol, ethanol, propanediol, butylene glycol, dipropylene glycol, ethoxylated or propoxylated glycols, cyclic polyols or any mixture of these solvents. The diluted active agent is then sterilized by sterile filtration.

After this stage, the peptide hydrolysate of pea is characterized by a peptide compound content of 0.5 to 5.5 g/l. This peptide hydrolysate corresponds to the active agent according to the invention.

After this dilution stage, the active agent can be encapsulated or contained in a cosmetic or pharmaceutical carrier such as liposomes or any other microcapsule used in the field of cosmetics or adsorbed onto powdery organic polymers or mineral supports such as talc and bentonites.

The second aspect of the invention is the use of a cosmetic composition comprising an effective quantity of a peptide hydrolysate of pea according to the invention as an active agent, in a physiologically acceptable medium, to maintain or restore cutaneous moisturization.

According to this particular aspect of the invention, the peptide hydrolysate of pea is also used as an active agent in a cosmetic composition to combat cutaneous dryness.

According to an advantageous embodiment of the invention, the active agent according to the invention is present in the compositions of the invention in an effective quantity, that is to say in a concentration of between approximately 0.0001% and 20% and preferably in a concentration of between approximately 0.05% and 5% relative to the total weight of the final composition.

The composition that can be used according to the invention will be able to be applied in any appropriate manner, in particular orally, parenterally or topically, and the formulation of the compositions will be adapted by the person skilled in the art, in particular for cosmetic or dermatological compositions. The compositions according to the invention are advantageously designed to be administered topically. These compositions must therefore contain a physiologically acceptable medium, i.e. compatible with the skin and epithelial appendages, and cover all cosmetic or dermatological forms.

These compositions can specifically exist in the form of an aqueous, hydroalcoholic or oily solution; oil-in-water emulsion, water-in-oil emulsion or multiple emulsions; these can also exist in the form of creams, suspensions or even powders adapted for application on the skin, mucus membranes, lips and/or epithelial appendages. These compositions can also be more or less fluid and have the appearance of a cream, a lotion, a milk, a serum, a pomade, a gel, a paste or a mousse. They can also exist in solid form, as a stick, or can be applied to the skin as an aerosol. They can also be used as a skincare product and/or as a makeup product.

Furthermore, this set of compositions comprises any conventionally used additive envisaged in the scope of application as well as necessary additives for their formulation, such as co-solvents (ethanol, glycerol, benzyl alcohol, damper . . . ), thickeners, thinners, emulsifiers, antioxidants, colorants, solar filters, pigments, fillers, preservatives, perfumes, odor absorbers, essential oils, oligoelements, essential fatty acids, surfactants, film-forming polymers, chemical filters or minerals, moisturizing agents or thermal waters etc. Water-soluble, preferably natural, polymers, such as polysaccharides or polypeptides, cellulose derivatives of the type methylcellulose or hydroxypropylcellulose, or even synthetic polymers, poloxamers, carbomers, siloxanes, PVA or PVP, and in particular polymers sold by the company ISP, can be cited, for example.

In every instance, the person skilled in the art will ensure that these additives and proportions thereof are selected in such a way as to not be detrimental to the desired advantageous properties of the composition according to the invention. These additives can, for example, be present in concentrations from 0.01% to 20% of the total weight of the composition. When the composition of the invention is an emulsion, the fatty phase can represent from 5 to 80% in weight, and preferably from 5 to 50% in weight relative to the total weight of the composition. The emulsifiers and co-emulsifiers used in the composition are to be selected from those which are typically used in the relevant field. For example, they can be used in a proportion from 0.3 to 30% in weight, relative to the total weight of the composition.

It is well understood that the active agent according to the invention can be used on its own or in conjunction with other active ingredients.

Furthermore, the compositions which can be used according to the invention advantageously contain at least one other active agent designed to promote the way in which the active agent according to the invention acts. The following types of ingredients can be cited, in a non-limiting manner: other peptide active agents, vegetable extracts, healing agents, anti-ageing agents, anti-wrinkle agents, soothing agents, anti-free radicals, anti-UV agents, agents for stimulating dermal macromolecular synthesis or energetic metabolism, moisturizing agents, antibacterial agents, antifungal agents, anti-inflammatories, anesthetics, agents modulating cutaneous differentiation, cutaneous pigmentation or depigmentation, and agents for stimulating nail and hair growth.

It is preferable for an anti-free radical or antioxidant agent, or an agent stimulating dermal macromolecular synthesis or energetic metabolism, to be used. In a more particular embodiment, the composition according to the invention will comprise, as well as peptide hydrolysate of pea, at least one cytochrome c-activating compound, and/or;
at least one moisturizing compound such as an aquaporin-activating compound, and/or;
at least one sirtuin-activating compound, and/or;
at least one compound for improving cellular adhesion, and/or;
at least one compound for improving the production of matrix proteins such as collagen, fibronectin, laminin, glycosaminoglycans, and/or;
at least one compound for modulating proteasome activity, and/or;
at least one compound for modulating circadian rhythm, and/or;
at least one compound for modulating HSP proteins, and/or;
at least one compound for increasing cellular energy, and/or;
at least one compound for modulating skin pigmentation, and/or;
at least one compound for activating the co-enzyme Q10, and/or;
at least one compound for improving barrier function, such as a compound for activating transglutaminase or HMG-CoA reductase.
at least one compound for protecting mitochondria.

The abovementioned compounds can be natural, such as peptide hydrolysates of plants, or also synthetic, such as peptide compounds.

The third object of the invention is a cosmetic treatment process designed to restore the water imbalance which occurs during cutaneous ageing, characterized in that a composition comprising a peptide hydrolysate of pea according to the invention is applied topically on the skin which is to be treated.

The fourth object of the invention is the use of an effective quantity of peptide hydrolysate of pea (*Pisum sativum* L.) as a moisturizing active agent for the preparation of a pharmaceutical composition designed to prevent or treat pathological dryness of the skin.

According to this form of the invention, the compositions are suitable to be administered orally for pharmaceutical use. Thus the compositions can in particular be in the form of tablets, liquid capsules, powder capsules, chewable gums, powders for swallowing such as they are, or mixed extemporaneously with, a liquid, syrups, gels and any other form known to the person skilled in the art. These compositions furthermore comprise any additive which is typically used in the envisaged scope of application, as well as the additives which are necessary for their formulation, such as solvents, thickeners, thinners, antioxidants, preservatives, other active pharmaceutical ingredients, essential oils, vitamins, essential fatty acids, etc.

The embodiments which are specific to this cosmetic treatment process also result from the above description. Further advantages and characteristics of the invention can be seen in greater detail by reading the illustrative, non-limiting examples provided.

Example 1

Preparing a Peptide Hydrolysate of Pea (*Pisum sativum* L.)

Peptide hydrolysate is obtained from a plant extract of the species *Pisum sativum* L. In a first stage, 1 kg of shelled peas is delipidated using an organic solvent: hexane. The thus-obtained ground pea is placed in a solution in 10 volumes of water in the presence of 2% POLYCLAR® 10 (polyvinylpolypyrrolidone-PVPP-insoluble). The mixture is adjusted to a pH value of between 7 and 8 with 1M aqueous soda solution.

After the pH has been adjusted, 2% of Flavourzym® is added to the reaction medium. The hydrolysate is obtained after having been stirred for 2 hours at 50° C. Then the enzyme is deactivated by heating the solution to 80° C. for 2 hours. The thus-obtained reaction mixture corresponds to a raw pea extract.

The purification process begins by successive filtrations using Seitz-Orion filters of decreasing porosity (up to 0.2 μm) so as to obtain a clear, bright solution. At this stage, the hydrolysate of pea is characterized by a dry weight of 70-80 g/kg, a protein level of 55-65 g/l, a sugar level of 2-5 g/l and a polyphenol level of 1-3 g/l.

The protein ingredient of this hydrolysate is identified by polyacrylamide gel electrophoresis. For this analysis, NuPAGE® Bis-Tris Pre-cast (Invitrogen) gels are used. The peptide hydrolysate of pea is heated to 70° C. for 10 minutes in reductive denaturing conditions in a NuPAGE® LDS sample buffer. A NuPAGE® Antioxidant solution is added to the inner chamber (cathode) so that the reduced proteins do not re-oxidize during electrophoresis. Protein migration is carried out using the NuPAGE® MES running buffer with standard SeeBlue Plus2 as a marker for molecular weight. Protein staining is carried out using Coomassie® Brilliant Blue R-250. In these conditions, 2 large protein families are observed: the first family corresponds to proteins with a molecular weight of 25 to 20 kDa and the second family corresponds to proteins with a molecular weight of less than 5 kDa.

This solution is then purified by eliminating the proteins with a molecular weight of greater than 5 kDa using cross-flow filtration.

For this, the hydrolysate of pea is pumped under pressure through a Pellicon® support equipped with a Pellicon® 2 Biomax-30 kDa cassette. The first filtrate is collected so as to then be filtered through another Pellicon® 2 Biomax-5 kDa cassette. When purification is complete, a yellowy-beige, clear and bright peptide hydrolysate of pea is obtained. It is characterized by a dry weight of 50 to 55 k/kg and a protein content of 50 to 52 g/l.

The next stage is the dilution phase in a water-glycerol mixture. The diluted active agent is then sterilized by sterile filtration. After this stage, the peptide hydrolysate of pea is characterized by a protein content of approximately 2.5 g/l.

Example 2

Identifying the Stimulating Effect of the Extract of Pea According to Example 1 Regarding Aquaporin Expression The purpose of this study is to determine the influence of the hydrolysate of pea according to example 1 regarding aquaporin-3 expression in normal human keratinocytes (NHKs).

Method:

NHKs are cultured in LabTek® slides until 80% are confluent, and are then treated with hydrolysate of pea according to example 1 at 0.5% or 1% for 24 hours.

Immunolabeling is then carried out using a polyclonal goat antibody specific to aquaporin-3 (Tebu Santa Cruz, sc-9885), then a secondary antibody coupled to a fluorescent marker. The cells are then examined by an epi-fluorescence microscope (Nikon Eclipse E600 microscope).

Results:

The microscopic observations show a stronger fluorescence in cells treated with the hydrolysate of pea according to example 1 at 0.5% and 1%.

Conclusions:

The hydrolysate of pea according to example 1 increases aquaporin-3 expression in human keratinocytes.

Example 3

Studying Pro/Filaggrin Expression in Human Skin Biopsies in the Presence of Hydrolysate of Pea According to Example 1

The purpose of this study is to determine the influence of the hydrolysate of pea according to example 1 regarding the quality of filaggrin and profilaggrin present in human skin biopsies.

Method:

Human skin samples are cultured in an air-liquid interface. The samples are treated with the hydrolysate of pea according to example 1 at 0.5% and 1% for 24 hours. These skin samples are then set with formaldehyde and then contained in paraffin. Sections of 4 μm are then produced. The immunolabeling is carried out after revealing specific sites by pepsin incubation. The immunolabeling is then carried out using a monoclonal mouse antibody specific to filaggrin (Tebu Santa Cruz, sc-66192)), then a secondary antibody coupled to a fluorescent marker. The sections of skin are then examined by an Epi-fluorescent microscope (Nikon Eclipse E600 microscope).

Results:

Less intense profilaggrin labeling is observed on the biopsies which were treated with hydrolysate of pea according to example 1, compared to untreated skin biopsies.

Conclusion:

The hydrolysate of pea according to example 1 enabled an increase in profilaggrin and filaggrin expression in skin.

Example 4

Studying Glycosaminoglycan Expression in Human Skin Biopsies in the Presence of the Hydrolysate of Pea According to Example 1

The purpose of this study is to determine the influence of the hydrolysate of pea according to example 1 on the quantity of glycosaminoglycans (GAGs) in human skin biopsies.

Method:

Human skin samples are cultured in an air-liquid interface. The samples are treated with the hydrolysate of pea according to example 1 at 0.5% for 48 hours. These skin samples are then set with formaldehyde and then contained in paraffin. Sections of 4 µm are then produced. Glycosaminoglycan staining is done using a colloidal iron solution, then a reaction with ferrocyanide-hydrochloric acid, which serves to stain the GAGs blue.

Results:

An increase in GAG expression is observed on the biopsies treated with the extract.

Conclusion:

The hydrolysate of pea according to example 1 enabled an increase in glycosaminoglycan expression in skin.

Example 5

Evaluating the Protective Effect of the Hydrolysate of Pea According to Example 1 as Regards Induced Cutaneous Drying The purpose of this study is to determine the protective effect of the hydrolysate of pea according to example 1 as regards ex-vivo cultures that undergo stress by induced cutaneous drying.

Method:

Human skin biopsies are kept ex-vivo in culture for 24 hours and treated with a solution at 0.5% or 1% of hydrolysate of pea according to example 1. The biopsies are then subjected to drying by ventilation for 3 hours. These skin samples are then set with formaldehyde and then contained in paraffin. Sections of 4 µm are then produced. Histological hematoxylin-eosin (H&E) staining enables the quality of cutaneous structures to be evaluated.

Results:

The controlled biopsies which are subjected to drying stress show characteristic signs of stress such as reduction in the thickness of the stratum corneum, the presence of edemas and disorganization of basal keratinocytes. The skin samples which were dried and treated with the hydrolysate of pea according to example 1 show a clear decrease in signs of cellular stress and an improved preservation of cutaneous structures, compared to untreated skin biopsies. On the other hand, the stratum corneum shows typical signs of improved moisturization compared to untreated skin biopsies.

Conclusion:

The hydrolysate of pea according to example 1 effectively protects the skin from drying-induced stress.

Example 6

Preparing the Compositions

1—Day Cream

| Commercial names | INCI Names | Mass % |
|---|---|---|
| PHASE A | | |
| MONTANOV 68 | Cetearyl Alcohol (and) Cetearyl Glucoside | 5.00 |
| JOJOBA OIL | Simmondsia Chinensis (Jojoba) | 3.00 |
| VASELINE OIL | ParaffinumLiquidum (Mineral Oil) | 2.00 |
| SQUALANE | Squalane | 3.00 |
| CERAPHYL 368 | Ethylhexyl palmitate | 4.00 |
| CERAPHYL 41 | C12-C15 Alkyl Lactate | 3.00 |
| RAPITHIX A-60 | Sodium polyacrylate (and) Hydrogenated Polydecene (and) Trideceth -6 | 0.30 |
| PHASE B | | |
| GLYCERIN | Glycerin | 5.00 |
| ALLANTOIN | Allantoin | 0.10 |
| DEMINERALIZED WATER | Aqua (Water) | qs 100 |
| PHASE C | | |
| ROKONSAL MEP | Phenoxyethanol (and) Methylparaben (and) Ethylparaben (and) Propylparaben | 0.50 |
| PHASE D | | |
| ACTIVE AGENT ACCORDING TO EXAMPLE 1 | | 5% |
| PHASE E | | |
| FRAGRANCE | Parfum (Fragrance) | qs |

Method:

Weigh the ingredients from the fatty phase and heat to 70° C. while stirring. Prepare phase B and heat it to 70° C. Emulsify phase A into phase B. Add phase D at approximately 50° C. while stirring. When it is below 40° C., add the active agent (phase D). Aromatize and chill to ambient temperature.

2. O/W Moisturizing Cream

| Commercial Names | INCI Names | Mass % |
|---|---|---|
| PHASE A | | |
| ARLACEL P 135 | PEG-30 Dipolyhydroxystearate Isononanoate | 2.00 |
| CERAPHYL 375 | Isostearyl Neopentanoate | 3.00 |
| PANALANE L-14E | Hydrogenated Polyisobutene | 3.00 |
| CERAPHYL ODS | Octyldodecyl Stearate | 9.00 |
| CERAPHYL 368 | Ethylhexyl Palmitate | 3.00 |
| PHASE B | | |
| DEMINERALIZED WATER | Aqua (Water) | qs 100 |
| ATLAS G-2330 | Sorbeth-30 | 4.00 |
| MAGNESIUM SULFATE 7H2O | Magnesium Sulfate | 0.70 |
| ACTIVE AGENT ACCORDING TO EXAMPLE 1 | | 2% |

-continued

| Commercial Names | INCI Names | Mass % |
|---|---|---|
| PHASE C | | |
| LIQUAPAR OPTIMA | Phenoxyethanol (and) Methylparaben (and) Isopropylparaben (and) Isobutylparaben (and) Butylparaben | 0.50 |
| PHASE D | | |
| FRAGRANCE | Parfum (Fragrance) | qs |

Method:

Weigh phase A and heat to 70° C. while stirring. Prepare phase B and heat it to 75° C. Emulsify phase B into phase A while stirring vigorously with a rotor/stator.

Homogenize for several minutes. Rapidly chill using an iced water bath while stirring vigorously. Add phase C at roughly 50° C. and add the fragrance (phase D) at 40° C. Continue chilling until ambient temperature is reached.

3—Moisturizing lotion

| Commercial Names | INCI Names | Mass % |
|---|---|---|
| DEMINERALIZED WATER | Aqua (Water) | qs 100 |
| GLYCERIN | Glycerin | 2.00 |
| PROPYLENE GLYCOL | Propylene Glycol | 2.00 |
| GLUCAM E-10 | Methyl Gluceth -10 | 1.00 |
| NEOSORB | Sorbitol | 5.00 |
| ALLANTOIN | Allantoin | 0.10 |
| ROKONSAL BSB | Benzoic Acid (and) Sorbic Acid (and) Benzyl Alcohol | 0.30 |
| ACTIVE AGENT ACCORDING TO EXAMPLE 1 | | 0.5% |
| Water-soluble FRAGRANCE | Parfum (Fragrance) | qs |

Method:

Add the ingredients individually to the necessary quantity of water and stir until they are completely dissolved. Readjust the pH to roughly 5.5, if necessary. Add the active agent at the end of the formulation. Aromatize with a water-soluble fragrance while stirring gently.

The invention claimed is:

1. A method of maintaining or restoring cutaneous moisturization by improving the capacity for storing water in the corneal layer, the basal layers of the epidermis, and the dermis, the method comprising:
    obtaining a peptide hydrolysate of pea (*Pisum sativum* L.) from shelled peas delipidated by using hexane, extracted in water comprising insoluble polyvinylpolypyrrolidone (PVPP), and hydrolysed by a protease from *Aspergillus* at a pH between 7 and 8, the peptide hydrolysate comprising, after filtration, a dry weight of 70-80 g/kg, a protein level of 55-65 g/l, a sugar level of 2-5 g/l and a polyphenol level of 1-3 g/l, said peptide hydrolysate thus obtained being purified and diluted in a water-glycerol mixture to comprise about 0.5 g/l to about 5.5 g/l of peptides having a molecular weight of less than 5 kDa, the proteins with a molecular weight of greater than 5 kDa being eliminated,
    providing a cosmetic composition comprising:
        about 0.5% to about 1% in weight relative to the total weight of the composition of an effective quantity of the purified and diluted peptide hydrolysate of pea (*Pisum sativum* L.), as a skin-moisturizing active agent, and
        a physiologically acceptable medium; and
    applying the cosmetic composition to a treatment area of a subject in need thereof.

2. The method according to claim 1, wherein the cosmetic composition treats cutaneous dryness.

3. The method of claim 1, wherein the composition is in a form adapted for topical application.

4. A cosmetic treatment process designed to restore the water imbalance which occurs during cutaneous ageing, the method comprising:
    obtaining a peptide hydrolysate of pea (*Pisum sativum* L.) from shelled peas delipidated by using hexane, extracted in water comprising insoluble polyvinylpolypyrrolidone (PVPP), and hydrolysed by a protease from *Aspergillus* at a pH between 7 and 8, the peptide hydrolysate comprising, after filtration, a dry weight of 70-80 g/kg, a protein level of 55-65 g/l, a sugar level of 2-5 g/l and a polyphenol level of 1-3 g/l, said peptide hydrolysate thus obtained being purified and diluted in a water-glycerol mixture to comprise about 0.5 g/l to about 5.5 g/l of peptides having a molecular weight of less than 5 kDa, the proteins with a molecular weight of greater than 5 kDa being eliminated,
    providing a composition comprising:
        about 0.5% to about 1% in weight relative to the total weight of the composition of an effective quantity of the purified and diluted peptide hydrolysate of pea (*Pisum sativum* L.), as a skin-moisturizing active agent, and
        a physiologically acceptable medium; and
    applying the composition topically to the skin of a subject in need thereof which is to be treated.

5. A method of treating pathological dryness of the skin, the method comprising:
    obtaining a peptide hydrolysate of pea (*Pisum sativum* L.) from shelled peas delipidated by using hexane, extracted in water comprising insoluble polyvinylpolypyrrolidone (PVPP), and hydrolysed by a protease from *Aspergillus* at a pH between 7 and 8, the peptide hydrolysate comprising, after filtration, a dry weight of 70-80 g/kg, a protein level of 55-65 g/l, a sugar level of 2-5 g/l and a polyphenol level of 1-3 g/l, said peptide hydrolysate thus obtained being purified and diluted in a water-glycerol mixture to comprise about 0.5 g/l to about 5.5 g/l of peptides having a molecular weight of less than 5 kDa, the proteins with a molecular weight of greater than 5 kDa being eliminated,
    administering a pharmaceutical composition to a mammal in need thereof, the pharmaceutical composition comprising:
        about 0.5% to about 1% in weight relative to the total weight of the composition of an effective quantity of the purified and diluted peptide hydrolysate of pea (*Pisum sativum* L.), as a skin-moisturizing active agent, and
        a physiologically acceptable medium.

6. The method of claim 1, wherein said peptide hydrolysate increases aquaporin expression.

7. The method of claim 6, wherein the aquaporin expression includes aquaporin-3.

8. The method of claim 1, wherein said peptide hydrolysate increases glycosaminoglycan expression.

9. The method of claim 1, wherein said peptide hydrolysate increases filaggrin expression.

* * * * *